(12) United States Patent
Ritsche

(10) Patent No.: US 10,363,566 B2
(45) Date of Patent: Jul. 30, 2019

(54) DISCHARGE HEAD FOR A DISPENSER FOR DISCHARGING A FLUID AND DISPENSER COMPRISING A DISCHARGE HEAD OF THIS TYPE AND SECURING SECTION FOR A DISCHARGE HEAD OF THIS TYPE

(71) Applicant: APTAR RADOLFZELL GMBH, Radolfzell (DE)

(72) Inventor: Stefan Ritsche, Eigeltingen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 0 days.

(21) Appl. No.: 15/564,282

(22) PCT Filed: Apr. 26, 2016

(86) PCT No.: PCT/EP2016/059320
§ 371 (c)(1),
(2) Date: Oct. 4, 2017

(87) PCT Pub. No.: WO2016/180633
PCT Pub. Date: Nov. 17, 2016

(65) Prior Publication Data
US 2018/0133731 A1 May 17, 2018

(30) Foreign Application Priority Data
May 13, 2015 (EP) .................... 15167614

(51) Int. Cl.
*B05B 11/00* (2006.01)
*A61M 15/08* (2006.01)
*A61M 11/00* (2006.01)

(52) U.S. Cl.
CPC ....... *B05B 11/0032* (2013.01); *A61M 11/007* (2014.02); *A61M 15/08* (2013.01); *A61M 2209/06* (2013.01)

(58) Field of Classification Search
CPC .... B65D 41/3423; B65D 41/62; B65D 41/12; B65D 47/122; B65D 47/123;
(Continued)

(56) References Cited

U.S. PATENT DOCUMENTS 3,462,045 A * 8/1969 Markowitz ............ B65D 83/40
222/153.1
3,526,343 A * 9/1970 O'Donnell .......... B05B 11/0027
222/182

(Continued)

FOREIGN PATENT DOCUMENTS

CN 104340501 A 2/2015
DE 2624900 A * 12/1977 ........... A61F 9/0008
(Continued)

OTHER PUBLICATIONS

Office Action of European Patent Office issued in European Application No. 15 167 614.5, dated Mar. 13, 2018 (5 pages).
(Continued)

*Primary Examiner* — Patrick M. Buechner
(74) *Attorney, Agent, or Firm* — Flynn Thiel, P.C.

(57) ABSTRACT

A discharge head for a dispenser including a base and an applicator mounted movably thereon. The base is fitted onto a liquid reservoir or is rigidly integrated on a liquid reservoir. The applicator includes a discharge opening through which liquid is released into an environment. The discharge head includes a pump mechanism or a valve mechanism arranged in a liquid channel connecting the liquid reservoir to the discharge opening. The pump mechanism is actuated by displacement of the applicator relative to the base, or the valve mechanism is opened and closed by displacement of the applicator relative to the base. The discharge head includes a cap unit with a cap for covering the discharge opening and a separate securing portion mounted securely (Continued)

on the base or the applicator via a securing mechanism and is designed to secure the cap releasably.

14 Claims, 7 Drawing Sheets

(58) Field of Classification Search
CPC .... B65D 47/125; B65D 47/126; B65D 47/18; B65D 50/02; B65D 50/04; B65D 50/041; B65D 50/043; B65D 50/045; B65D 50/046; B67B 2201/12; B05B 11/0027; B05B 11/0032; B05B 11/3059; A61M 15/08; A61M 15/0025; A61M 11/006; A61M 11/007; A61M 2209/06
See application file for complete search history.

(56) References Cited

U.S. PATENT DOCUMENTS

| | | | | |
|---|---|---|---|---|
| 3,706,401 | A * | 12/1972 | Gach | B65D 41/06 220/915 |
| 3,738,536 | A * | 6/1973 | Gach | B65D 83/40 215/220 |
| 3,747,807 | A * | 7/1973 | Gach | B65D 83/40 222/153.1 |
| 3,866,802 | A * | 2/1975 | Birrell | B65D 83/40 222/153.1 |
| 3,910,442 | A * | 10/1975 | Gargano | B65D 41/06 215/218 |
| 3,998,363 | A * | 12/1976 | Beres | B05B 11/0027 222/321.9 |
| 4,216,883 | A * | 8/1980 | Tasaki | B05B 11/0013 222/321.2 |
| 4,705,181 | A * | 11/1987 | Burke | B65D 50/041 215/213 |
| 4,746,035 | A * | 5/1988 | Anderson | B05B 11/0027 215/252 |
| 4,944,429 | A * | 7/1990 | Bishop | B05B 11/0027 222/153.13 |
| 5,509,580 | A * | 4/1996 | Glynn | B65D 50/046 222/153.1 |
| 5,657,905 | A * | 8/1997 | Glynn | B65D 50/046 215/216 |
| 6,290,103 | B1 * | 9/2001 | Fraillon | B65D 47/244 222/321.1 |
| 6,896,151 | B1 * | 5/2005 | Robinson | B65D 47/122 222/1 |
| 7,784,645 | B2 | 8/2010 | Carta | |
| 8,292,132 | B2 * | 10/2012 | Behar | B65D 83/38 222/153.1 |
| 9,718,074 | B2 | 8/2017 | Deng et al. | |
| 2002/0079338 | A1 * | 6/2002 | Pardo | B65D 47/18 222/422 |
| 2003/0173380 | A1 * | 9/2003 | Gerber | B65D 47/122 222/519 |
| 2009/0277930 | A1 | 11/2009 | Carta | |
| 2010/0308081 | A1 * | 12/2010 | Waitz | B05B 11/3059 222/153.01 |
| 2011/0094990 | A1 * | 4/2011 | Sprishen | B65D 50/041 215/217 |
| 2014/0014611 | A1 * | 1/2014 | Buehler | B65D 50/041 215/217 |
| 2014/0284299 | A1 * | 9/2014 | Barber | B65D 50/045 215/44 |
| 2016/0243319 | A1 * | 8/2016 | Szymiczek | B05B 11/0032 |

FOREIGN PATENT DOCUMENTS

| | | |
|---|---|---|
| DE | 10 2013 202 933 B3 | 11/2013 |
| EP | 0 653 359 A1 | 5/1995 |
| WO | WO 2008/001406 A1 | 1/2008 |

OTHER PUBLICATIONS

International Search Report issued in Application No. PCT/EP2016/059320 with English translation, dated Jul. 11, 2016 (5 pages).
Written Opinion of International Searching Authority issued in Application No. PCT/EP2016/059320 dated Jul. 11, 2016 (6 pages).
European Patent Office Search Report issued in Application No. 15 16 7614 with English translation of category of cited documents dated Oct. 26, 2015 (7 pages).

* cited by examiner

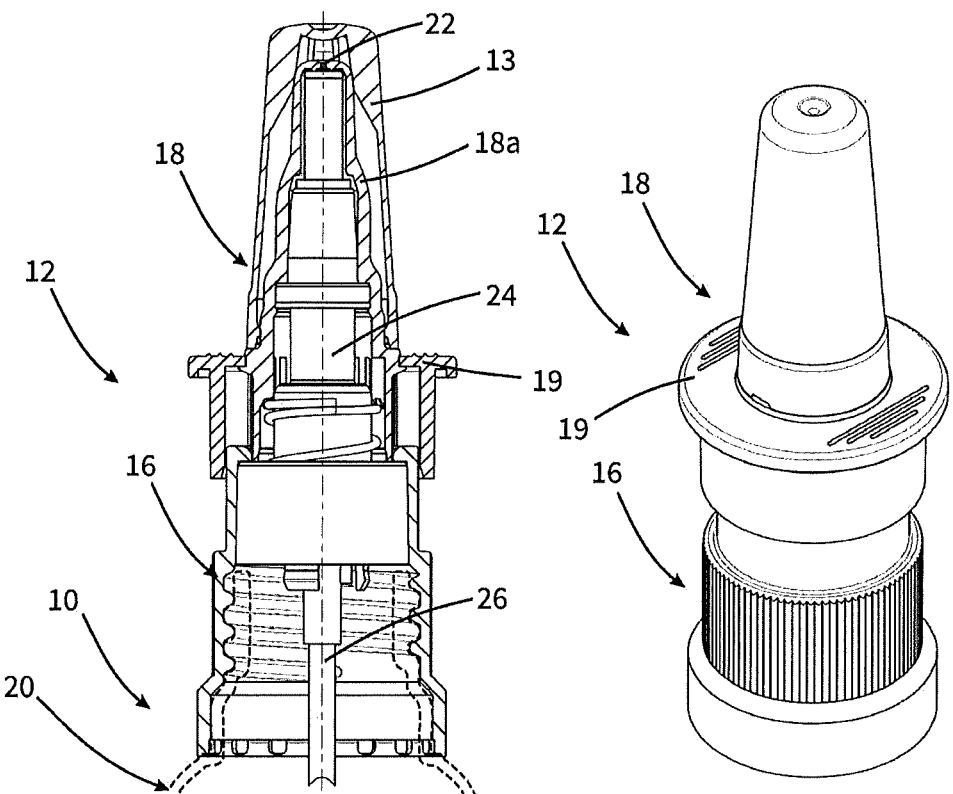
Fig. 1A
*Prior Art*
Fig. 1B
*Prior Art*
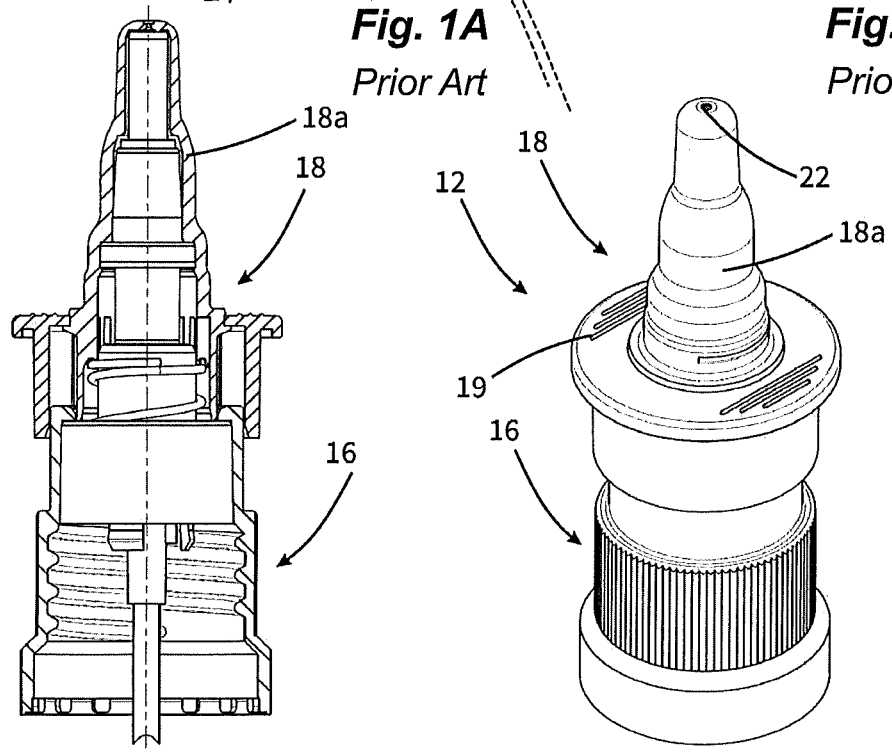
Fig. 1C
*Prior Art*
Fig. 1D
*Prior Art*

DISCHARGE HEAD FOR A DISPENSER FOR DISCHARGING A FLUID AND DISPENSER COMPRISING A DISCHARGE HEAD OF THIS TYPE AND SECURING SECTION FOR A DISCHARGE HEAD OF THIS TYPE

FIELD OF APPLICATION AND PRIOR ART

The invention relates to a discharge head for a dispenser for discharging a liquid, in particular for discharging a pharmaceutical or cosmetic liquid, according to the preamble of claim 1. The invention further relates to a cap unit therefor according to the preamble of claim 11. The invention further relates to a dispenser according to the preamble of claim 12.

Discharge heads of the type in question, and dispensers comprising such discharge heads, are generally known. They are used for discharging pharmaceutical liquids, for example for discharging medicaments or saline solutions. The dispensers of the type in question comprise an applicator which, when it is pressed down, causes liquid to be conveyed to the discharge opening and to be discharged into the environment.

Since dispensers of the type in question are used mainly for discharging pharmaceutical liquids, e.g. substances containing imidazoline, it is necessary to provide such dispensers with a childproofing means. This prevents a situation where small children are able to cause liquid to be discharged and thus have access to the possibly dangerous medicament.

Childproofing means on liquid dispensers are likewise known in many forms from the prior art. They mainly involve childproofing means that make it difficult to remove the cap or to actuate the dispenser. Such dispensers have usually already been suitably configured with childproofing means in the context of their development.

However, there are also many known dispenser models that were designed without such childproofing means. Given the regulations that govern childproofing means, such dispensers are usually not able to be used any further, such that a new design with a large number of new component parts is often needed.

Problem and Solution

The problem addressed by the invention is to make available a possibility by which dispensers, and the discharge heads of such dispensers, without childproofing means can be equipped as easily as possible with such childproofing means, such that a large number of component parts of the dispenser can remain unchanged.

The problem addressed by the invention is solved by a discharge head as claimed in claim 1.

The discharge head comprises a base and an applicator mounted movably on the base. The base is designed to be fitted onto a liquid reservoir or to be rigidly integrated on a liquid reservoir. The applicator comprises a discharge opening through which liquid can be released into an environment. The discharge head comprises a pump mechanism or a valve mechanism, which is arranged in a liquid channel connecting the liquid reservoir to the discharge opening, wherein the pump mechanism can be actuated by displacement of the applicator with respect to the base, or wherein the valve mechanism can be opened and closed by displacement of the applicator with respect to the base.

The discharge head comprises a childproof cap unit. The cap unit comprises a cap for covering the discharge opening. The cap unit further comprises a separate securing portion which, on the one hand, is mounted securely on the base or the applicator via a securing mechanism and, on the other hand, is designed to secure the cap releasably.

The discharge head according to the invention thus has a cap which is designed to make it difficult for children to gain access to the discharge opening. This cap is made secure on the applicator, this being effected directly via said securing portion. The design of the applicator can thus remain unchanged from an applicator that is not provided with childproofing means. It is only when the securing portion of the cap unit is applied that a component is made available which, together with the cap, allows it to be fastened to the applicator in a childproof manner.

This means that the discharge head is already fully functional in terms of its main function, that of liquid discharge, without the cap unit according to the invention being provided. The cap unit simply supplements the childproofing function and can be omitted when no such childproofing function is needed.

The separate securing portion is connected to the applicator via the securing mechanism. This securing is intended to be so stable that a child cannot release it. The childproofing is favored by the fact that the two-part design, with the applicator on the one hand and the securing portion on the other hand, need not be apparent to the child. The child will therefore try to release the cap from the securing portion rather than releasing the entire cap unit from the applicator.

A design is regarded as advantageous in which the securing portion is provided on the applicator, and thus on the component movable with respect to the base of the discharge head. In principle, however, it is also possible that the cap covers the entire applicator and is secured on a securing portion which for its part is connected rigidly to the base. Where the rest of the description refers to the cap unit being secured on the applicator, this also means the alternative in which the securing takes place on the base.

On its inside, the cap can have a sealing surface by means of which the discharge opening is directly closed when the cap is fitted. In this way, it is possible to particularly reliably prevent children from gaining access to the liquid since, even if the dispenser is actuated with the cap fitted, the liquid does not reach into the cap interior downstream from the discharge opening.

The cap can also have a blocking portion which, together with a further blocking portion on the base, prevents the applicator from being pressed down with respect to the base when the cap is fitted. In such a design, liquid is therefore already prevented from being conveyed in the direction of the discharge opening. It is also thus possible to effectively prevent liquid from getting into the cap interior downstream from the discharge opening.

The securing portion of the cap unit can be designed as a body which is sleeve-shaped at least in part and is open at both ends and surrounds the applicator.

The sleeve shape of the securing portion is provided in order to be able to push the latter onto the applicator in particular from the direction of the discharge opening, this preferably already being done at the time of production. Although the sleeve could also be designed with slits, it is preferably closed all the way round. This allows it to be secured particularly firmly on the applicator or, if appropriate, also on the base and thereby prevent a separation of the securing portion from the applicator or the base. The sleeve shape also makes it possible to conceal the nature of the securing portion as a separate component.

The securing portion and the cap of the cap unit can be provided with a thread mechanism or a bayonet mechanism for securing the cap on the securing portion.

The thread mechanism or the bayonet mechanism dictates that the separation of the cap from the securing portion has to entail a combined rotational and translational movement. For small children, this already provides better protection than a cap that can simply be pulled off. However, such a thread mechanism or bayonet mechanism is preferably only a part of the childproofing, which includes other obstacles for children. In connection with the invention, a thread mechanism is understood as any guide surface which is inclined with respect to the main direction of extent of the applicator and which necessitates a simultaneous rotational and linear movement of the cap relative to the securing portion for the purposes of separation.

In other embodiments, however, it is also possible to do without a thread mechanism, for example in the case of a cap which can be separated from the securing portion by a purely translational movement, or in the case of a cap which can be decoupled by rotation in order then to be pulled off in a translational movement. The securing portion and the cap of the cap unit can have an anti-rotation mechanism, by means of which the cap and the securing portion can be secured against rotation, by form-fit engagement, in a defined rotation position. The securing portion or the cap can be deformable in part, in such a way that the rotation block that can be produced by the anti-rotation mechanism is releasable.

After the cap has been fitted on the securing portion, such an anti-rotation mechanism prevents an unimpeded relative rotational movement of the kind needed for the separation, for example, of a thread. Therefore, the anti-rotation mechanism first of all has to be released in order thereafter to be able to separate the cap from the securing portion by an at least also relative rotational movement. It is particularly preferable if the anti-rotation mechanism is released by a radial deformation of the cap or, if appropriate, also of the securing portion.

The securing portion is preferably provided with radial indents or protuberances which, in the rotationally secured state, receive corresponding protuberances or indents on the cap. Since, proceeding from the screwed-on state, only a rotational movement in the direction of unscrewing is needed, it is possible, instead of the indents and protuberances, to use abutment surfaces that restrict only in one direction of rotation.

The disengagement for the purpose of subsequent rotation is preferably achieved by the fact that the cap is pressed together at an offset of 90° with respect to these protuberances and indents or to abutments lying opposite each other, such that said disengagement takes place.

The cap can be designed as a double cap with an inner cap and an outer cap. In this case, the inner cap and the outer cap can have interacting coupling means by which a temporary rotation block between the outer cap and the inner cap can be produced when force is applied to the outer cap.

In such a configuration, the inner cap and the outer cap are in principle rotatable relative to each other, but they are not separable from each other, at least not when used as intended. When a radial or axial force is applied to the outer cap, the latter is brought into force-fit or in particular form-fit engagement with the inner cap, such that joint rotation is possible. This childproofing concept is known per se and has proven advantageous. In such a configuration, the securing portion can be of a comparatively simple design since, apart from thread turns, it does not require any further means in order to be connectable to said double cap.

The securing mechanism can comprise a latching connection mechanism.

A latching connection mechanism of this kind is a very simple way of fastening the securing portion to the applicator. Assembly is also very simple here, since the same procedure by which the preferably sleeve-shaped securing portion is pushed onto the applicator also brings about a joining of this latching mechanism toward the end of the relative movement.

The securing mechanism can be designed as a rotationally fixed securing mechanism, by which the securing portion, on the one hand, and the base or the applicator, on the other hand, are connected to each other for conjoint rotation.

The connection of the securing portion to the applicator, for conjoint rotation therewith, has the effect that application of a torque for authorized removal of the cap does not require gripping of the securing portion, on the one hand, and of the cap, on the other hand. Instead, the applicator or possibly also the base or the liquid reservoir, on the one hand, and the cap, on the other hand, can be gripped.

However, another configuration is also conceivable in which the securing portion is mounted so as to be intentionally rotatable on the applicator, such that a release of the cap in this case specifically requires a moment to be applied there. Depending on the design of the securing portion, this can represent a difficult obstacle for children.

The securing mechanism can be designed to couple the securing portion to the applicator, wherein the securing mechanism can comprise a radially outwardly open coupling groove, in which a coupling web provided internally on the securing portion engages.

A configuration in which an outwardly open groove is provided on the applicator, for securing the securing portion, has proven very advantageous. In this case, the coupling groove and the coupling web do not necessarily have to extend all about the circumference. If a sufficient deformability is provided in the course of assembly, however, a circumferential configuration may be advantageous. The advantage of such a configuration with coupling groove and coupling web is seen in particular when such a coupling groove is provided anyway on the applicator for securing a finger support. In the childproofed variant of the discharge head, this can be used for the securing portion, which in turn makes available a finger support.

The securing portion of the cap unit can have a gripping surface which, in order to increase the grippability, is provided with gripping ribs or other kinds of gripping elevations.

Such a gripping surface is advantageous in cases where the authorized release of the cap requires that the securing portion is gripped. This applies in particular to discharge heads which, in a non-childproofed variant, do not have any suitable surfaces for applying a torque that is needed to release the cap.

The securing portion of the cap unit can comprise a finger support, which preferably has an outer edge whose shape deviates from the shape of a circle.

The configuration of a securing portion with a finger support is recommended in particular when the finger support provided in a non-childproofed dispenser is intentionally omitted in order to create space for the securing portion. An outer edge that is not circular makes it easier for the user to grasp the finger support for the purpose of releasing the cap.

The applicator can be designed as a nasal applicator and have a nosepiece, at the distal end of which the discharge opening is provided.

Discharge heads with nasal applicators can be employed in particular for the use of nasally administered analgesics or imidazoline-containing or vaso-constrictive substances, for which childproofing is particularly important. In such discharge heads, the applicator is slim in parts, in order to permit insertion into the nostril of the patient. However, a slim design of this kind does not exclude the use of a sleeve-shaped securing portion. The wall of the latter can be sufficiently thin to still permit the slim design.

The applicator can be designed as an applicator for releasing drops and has a drop formation surface which surrounds the discharge opening and on which emerging liquid attaches itself until it detaches therefrom in the form of a drop.

On its outside, such an applicator has a preferably flat area which surrounds the discharge opening and which is surrounded by a tear-off edge. When the applicator is turned upside down, the liquid gathers here until the amount of liquid is sufficiently great to detach itself from the drop formation surface.

The applicator can have an external shape that narrows in the direction of the discharge opening, and the securing portion can have a shape that narrows on the inside in a manner corresponding to this shape of the applicator.

Such a configuration in which the inside of the securing portion bears flush on the inner applicator is particularly expedient for creating a slim applicator.

A circumferential sleeve portion which surrounds the base can be provided on the finger support.

Such a sleeve portion, which is preferably designed extending about the circumference, can extend from the finger support as part of the securing portion in the direction of the base and can thus prevent a situation where a child, attempting to discharge liquid, gets a finger caught between base and applicator.

The problem addressed by the invention is also solved by a cap unit as claimed in claim 11.

The cap unit has a securing portion for mounting on an applicator of the discharge head and has a cap for covering a discharge opening of the applicator. The securing portion is designed as a sleeve-shaped hollow body which is open at opposite ends in order to be pushed onto the applicator of the discharge head. The securing portion has latching means for producing a latched connection to the applicator of the discharge head. The cap and the securing portion are designed to be secured to each other releasably.

The cap unit according to the invention is composed of at least two components, namely the cap and the securing portion. These are the only components that have to be provided on a non-childproofed dispenser in order to render the latter childproof. Although the configuration of a discharge head according to the invention primarily has the aim of allowing the childproofing to be provided at the time of purchase of the dispenser, it is also conceivable for a cap unit according to the invention to be provided as a separate product which could be additionally acquired in order that a dispenser purchased without childproofing can be subsequently equipped with such childproofing.

The problem addressed by the invention is also solved by a dispenser as claimed in claim 12.

The dispenser comprises a liquid reservoir. The dispenser comprises a discharge head with a discharge opening through which liquid can be released into the environment. This discharge head is designed in the manner described above.

The discharge head and the liquid reservoir of such a dispenser can be designed as separate units which are connected, for example, by a thread, toothed housings, snap-in connections acting with form-fit engagement, or crimp connections.

However, designs are also conceivable in which the base of the discharge head is connected rigidly to the liquid reservoir or is connected rigidly to a housing inside which the liquid reservoir is provided. In this way, it can be made more difficult for a child to gain access to the liquid by separating the discharge head and the liquid reservoir.

The liquid contained in the dispenser is preferably a pharmaceutical or cosmetic medium. It is in particular in the form of analgesics or other kinds of pharmaceutical liquids that are harmful to children.

The liquid reservoir can have has a maximum volume of 1000 ml, preferably a maximum volume of 100 ml, particularly preferably a maximum volume of 50 ml.

BRIEF DESCRIPTION OF THE DRAWINGS

Further advantages and aspects of the invention will be gathered from the claims and from the following description of preferred illustrative embodiments of the invention, which are explained below with reference to the figures, in which:

FIGS. 1A to 1D show, by way of example, a known design of a dispenser for discharging liquid, in sectional and perspective views, with and without the cap.

FIGS. 2A and 2B show the discharge head according to this first illustrative embodiment in perspective views, with and without the cap.

FIG. 2C shows the discharge head according to this first illustrative embodiment in a sectional view.

FIGS. 2D to 2F show the securing portion of a cap unit of the discharge head according to this first illustrative embodiment, from above, from the side, and in a perspective view.

FIGS. 3A and 3B show the discharge head according to this second illustrative embodiment in perspective views, with and without the cap.

FIG. 3C shows the discharge head according to this second illustrative embodiment in a sectional view.

FIGS. 3D to 3F show the securing portion of a cap unit of the discharge head according to this second illustrative embodiment, from above, from the side, and in a perspective view.

FIGS. 4A and 4B show the discharge head according to this third illustrative embodiment in perspective views, with and without the cap.

FIG. 4C shows the discharge head according to this third illustrative embodiment in a sectional view.

FIGS. 4D and 4E show the securing portion of a cap unit of the discharge head according to this third illustrative embodiment, from above, from the side, and in a perspective view.

DETAILED DESCRIPTION OF THE ILLUSTRATIVE EMBODIMENTS

Figures 2A, 2B:
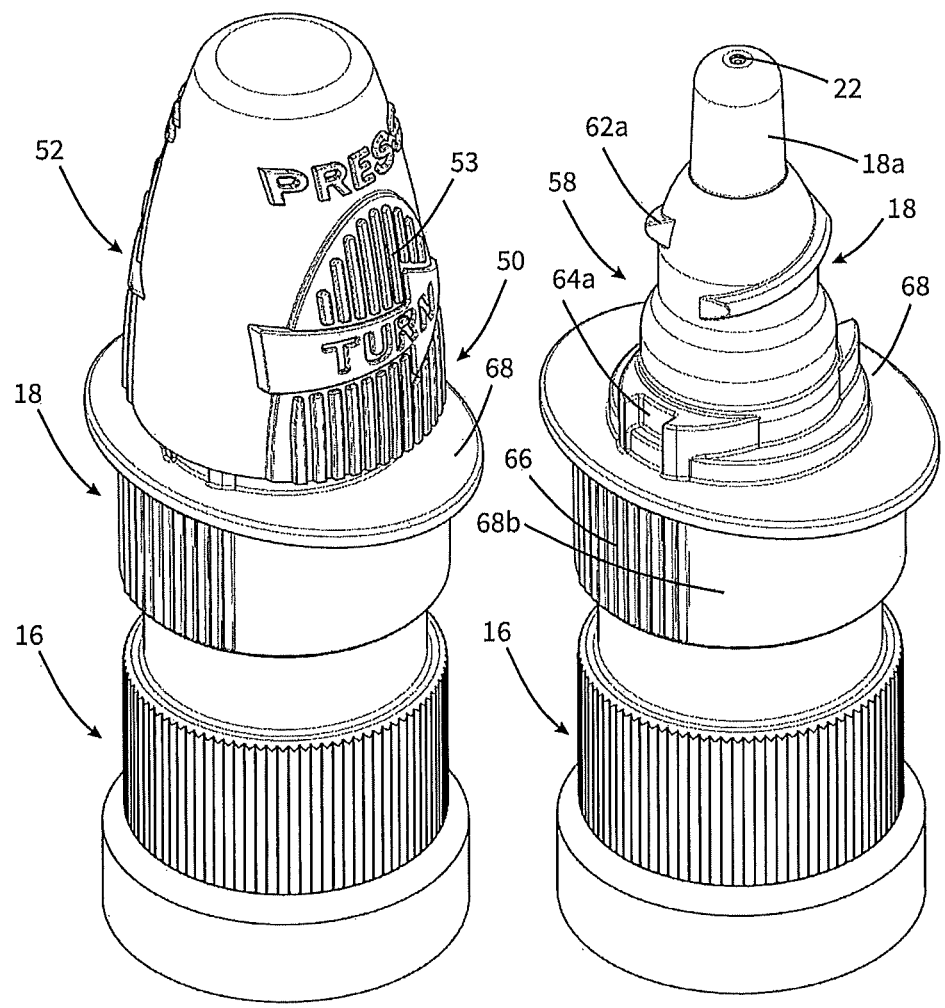
FIGS. 2A to 2F show a first illustrative embodiment of the invention.

FIGS. 1A to 1D show a discharge head 12 of a liquid dispenser 10, of which the liquid reservoir is indicated by broken lines in FIG. 1A for better understanding but has been omitted in the remaining figures for the sake of clarity.

A discharge head 12 of the kind in question is not childproof. The cap 13 of this dispenser 10 is simply fitted onto an applicator 18 of the discharge head 12, designed as a nosepiece, and is latched in place by force-fit engagement. Between a base 16 and the applicator 18 of the discharge head 12, a pump mechanism 24 is provided by means of which liquid can be conveyed from the liquid reservoir 20 through a liquid channel 26 as far as a discharge opening 22, when the applicator 18 is pressed down.

Instead of the pump mechanism 24, a valve mechanism could also be provided. In such a case, provision would be made that the liquid in the liquid reservoir 20 is already pressurized before the start of the discharge procedure and, as the valve mechanism is opened, flows in the direction of the discharge opening 22.

A dispenser as shown in FIGS. 1A to 1D represents a commercially established product. Accordingly, there are efficient tools available for producing the dispenser. In order to childproof such a dispenser, the invention affords the possibility of additionally providing this childproofing while maintaining all or almost all of the component parts of the dispenser according to FIGS. 1A to 1D. Apart from the fact that it is thus possible to avoid costs for new tools and for setting up a completely new production process, this also has the advantage that for several types of dispensers, whether childproofed or not childproofed, the number of parts is the same.

Figure 2C:
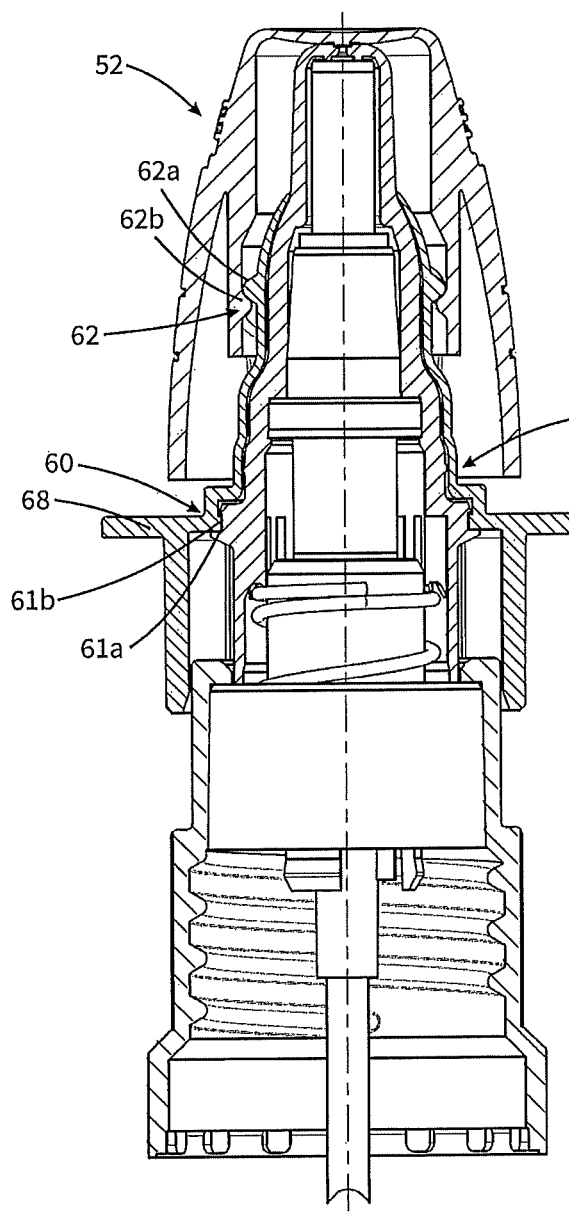

FIGS. 2A to 2F show a first variant of such childproofing provided on the dispenser of FIGS. 1A to 1D. In this variant, the cap 13 and a finger support 19 of the dispenser of FIGS. 1A to 1D are no longer used. All the other component parts remain and are unchanged. Referring in particular to FIG. 2C, this first embodiment of a dispenser according to the invention has a sleeve-shaped securing portion 58 which, together with a specially designed cap 52, forms a cap unit 50 according to the invention. The securing portion 58 is designed as a hollow body which is open at both ends and whose interior, in the area of a nosepiece 18a of the applicator 18, is adapted to the shape of this nosepiece 18a. On the inside of the securing portion 58, a coupling web 61b is provided which engages in an applicator-side coupling groove 61a and thus creates a latching connection. Said coupling groove 61a is the groove in which the finger support 19 was secured in the non-childproof dispenser of FIGS. 1A to 1D. The finger support 19 itself is replaced by a finger support 68 provided on the securing portion 58. This finger support 68, like the finger support 19, has a sleeve portion 68b which extends in the direction of the base 16 and partially surrounds the latter in the unpressed state, such that jamming of a finger is effectively prevented.

Figure 2D:
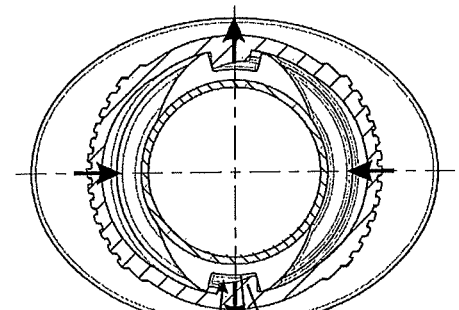
Figure 2E:
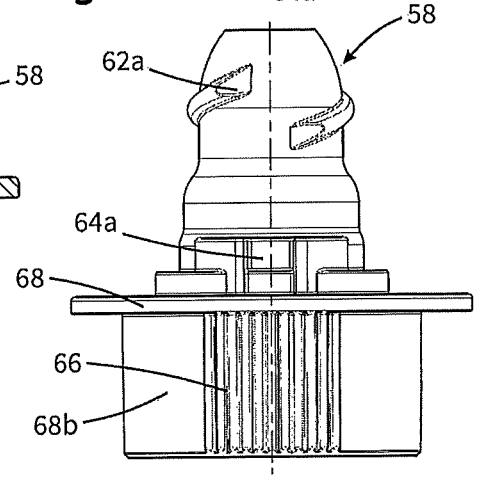
Figure 2F:
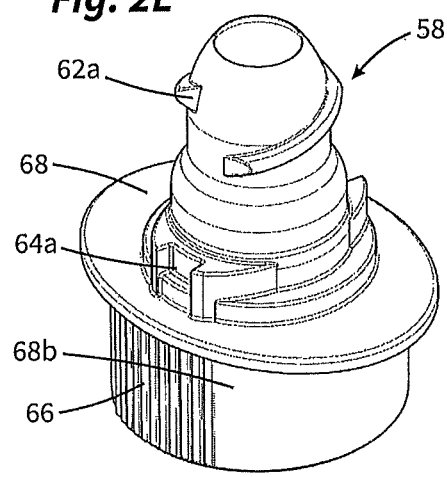
Figures 3A, 3B:
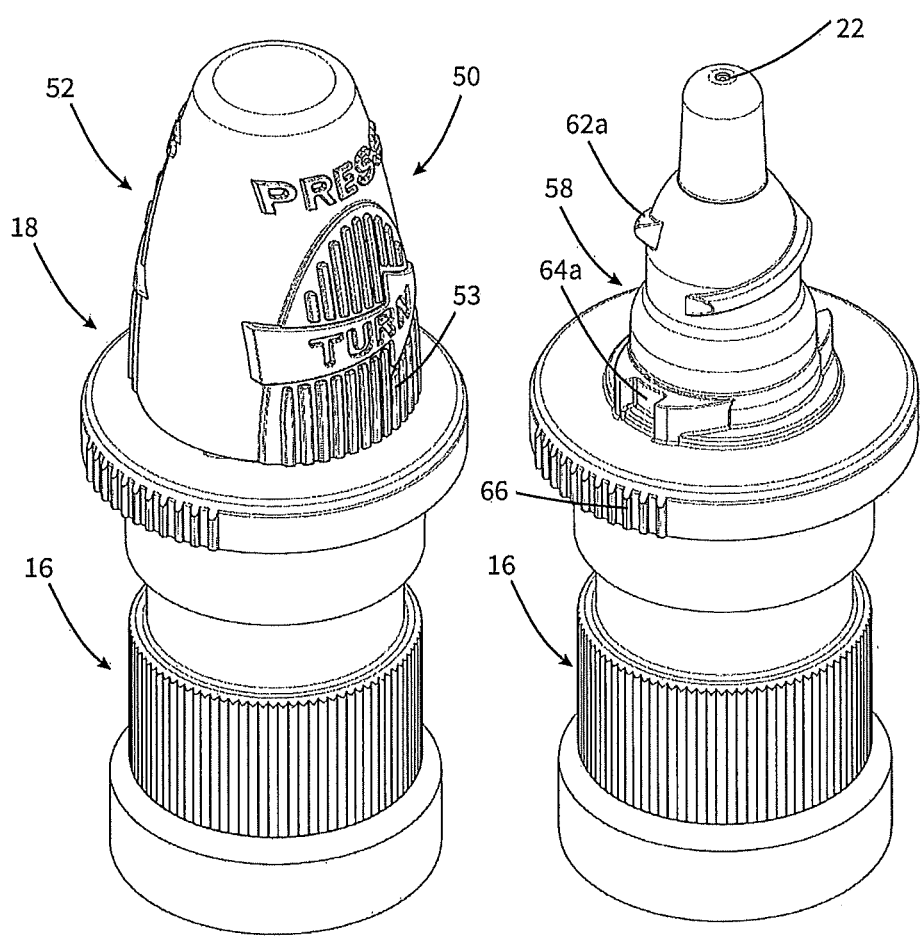
FIGS. 3A to 3F show a second illustrative embodiment of the invention.
Figures 3C, 3D, 3E, 3F:
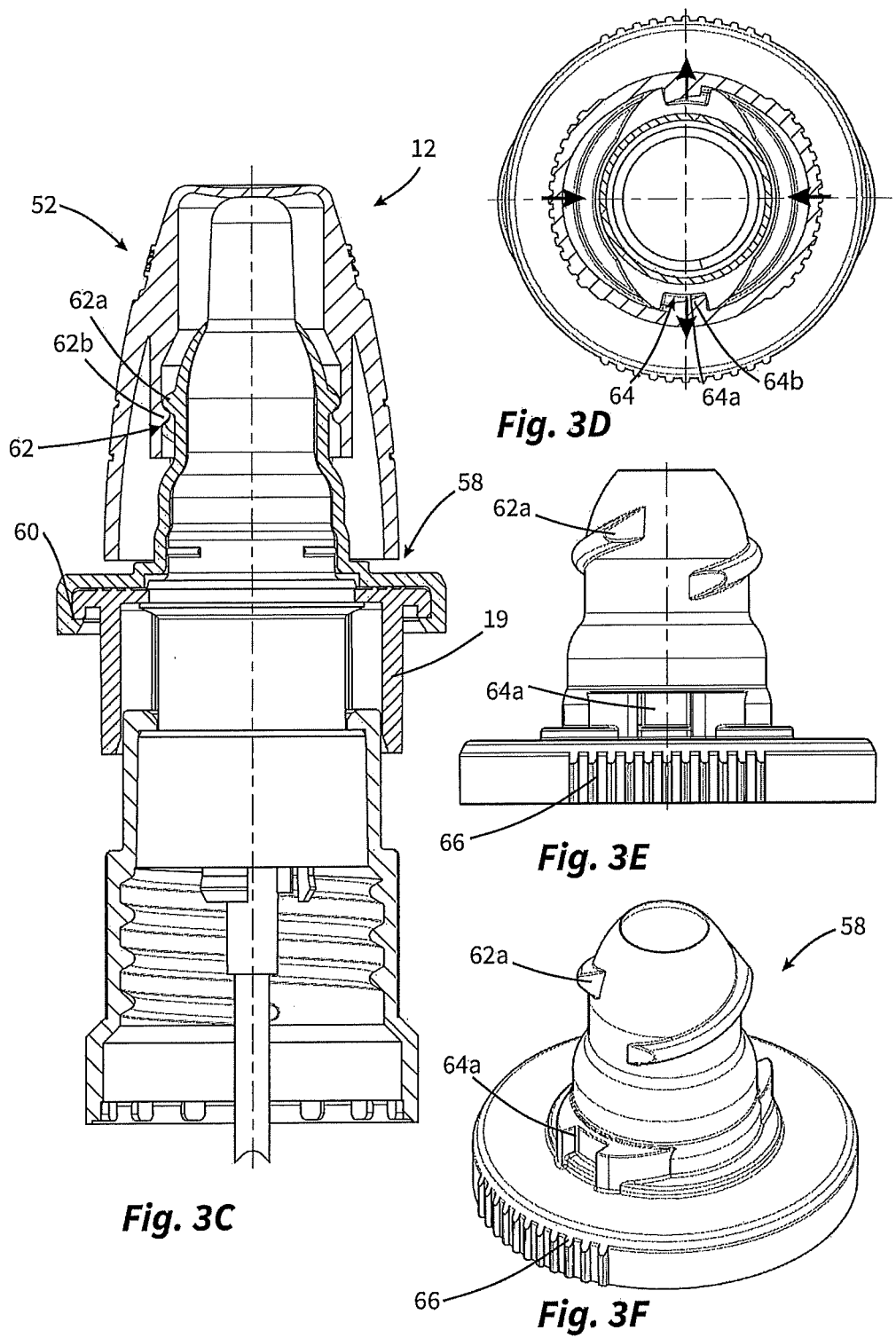
Figures 4A, 4B:
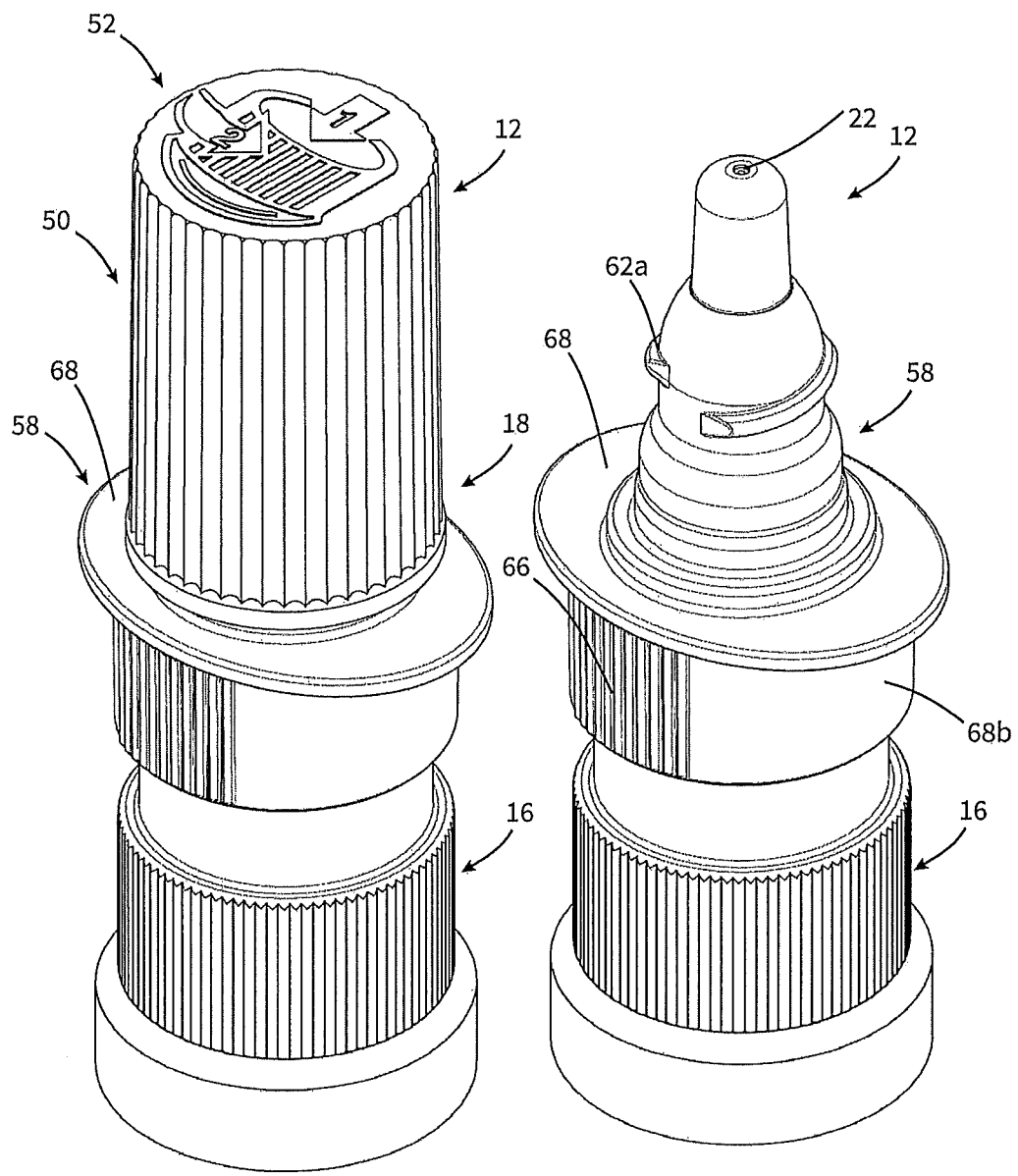
FIGS. 4A to 4E show a third illustrative embodiment of the invention.
Figures 4C, 4D, 4E:
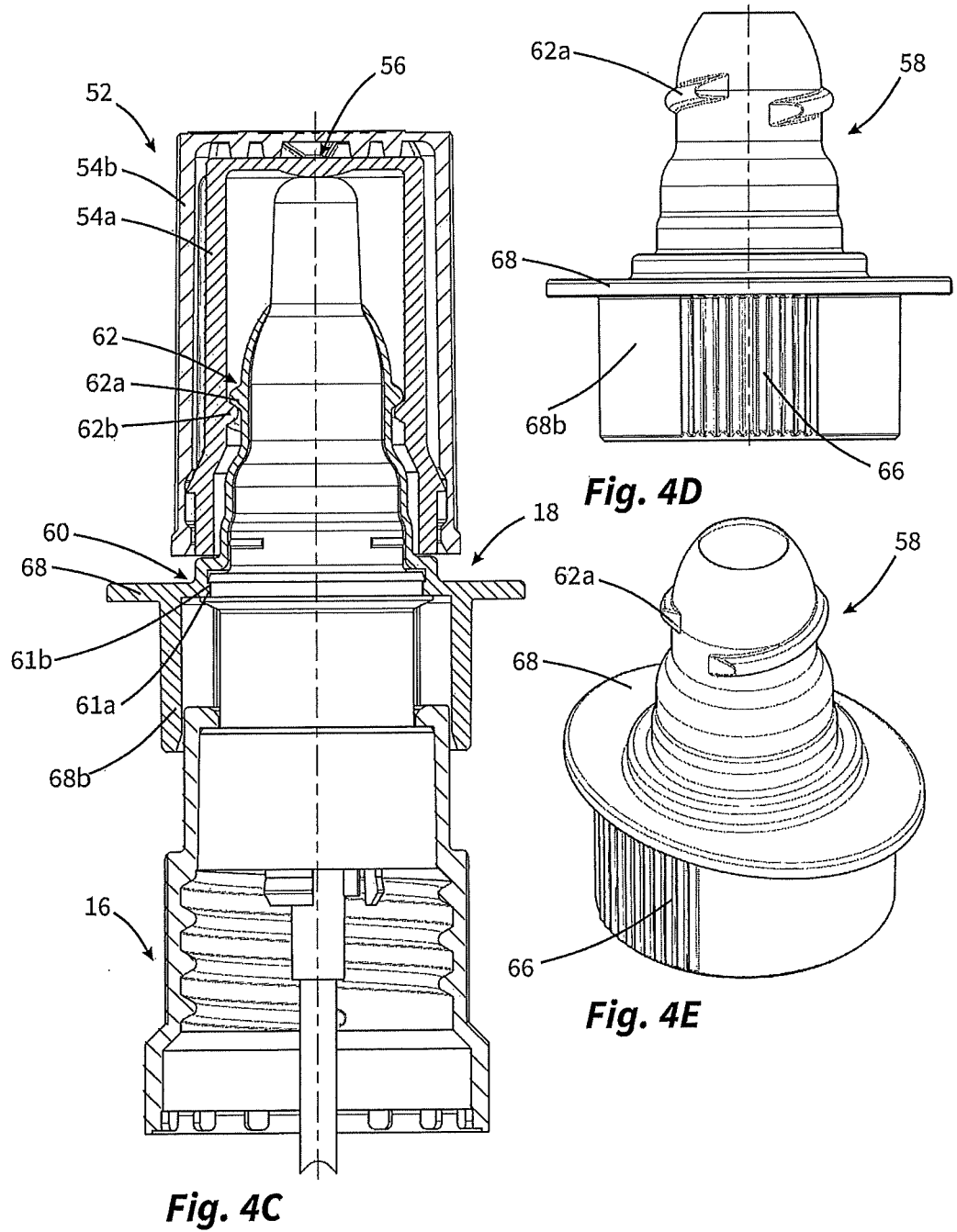

On the outside of the securing portion 58, the latter has a particular shape for allowing the cap 52 to be fastened in a childproof manner. This shape comprises an outer thread 62a, which is part of a thread mechanism 62, and also two recesses 64a, which are part of an anti-rotation mechanism 64. Corresponding to these, the inside of the cap 52 is provided with an inner thread 62b and two inwardly directed protuberances 64b. In the fitted state, which can be seen for example from FIG. 2A and is illustrated in FIG. 2D, the protuberances 64b are located in the recesses 64a and the outer thread 62a is in engagement with the inner thread 62b. To release the cap, two gripping surfaces 53 provided with gripping ribs on the cap 52 have to be pressed toward each other. In the manner illustrated by arrows in FIG. 2D, this leads to a disengagement of the protuberances 64b from the recesses 64a. In this way, the cap 52 can be unscrewed after it has been subjected to a force of this kind. To make this easier, the securing portion is also provided with gripping surfaces 66 at 90° to the gripping surfaces 53 in the fitted state of the cap 52. Compared to other kinds of gripping surfaces on the base or on the applicator, this arrangement of the gripping surfaces 66 in the securing portion has the advantage that a rotatability of the securing portion 58 with respect to the applicator 18 is not an obstacle to release of the cap. However, it is considered advantageous if the connection created in the area of the coupling groove 61a and of the coupling web 61b counteracts a rotation of the securing portion 58 with respect to the applicator 18. This can be achieved by a force-fit connection that can only be overcome with great force, or also by form-fit engagement if the coupling groove 61a permits such form-fit engagement in terms of rotation.

As will be seen from FIG. 2C, the inside of the end face of the cap 52 bears directly on the discharge opening in the fitted state of the cap, such that no liquid can escape. This ensures that no liquid gets into the area between cap 52 and discharge opening 22. Therefore, when the cap 52 is fitted, the actuation of the dispenser, i.e. the displacement of the applicator 18 with respect to the base 16, is also not possible.

The embodiment in FIGS. 3A to 3F is closely related to the embodiment of FIGS. 2A to 2F. The interaction between the securing portion 58 and the cap 52 of the cap unit 50 is identical to the preceding embodiment. The particular aspect of this configuration is that the securing portion does not replace the finger support 19 of the non-childproofed dispenser and instead engages around it in the manner shown in particular in FIG. 3C. An advantage of this is that, with the exception of the cap 13, the non-childproofed dispenser of FIGS. 1A to 1D can be fully assembled before the decision is made as to whether it is to be provided with childproofing. This further increases the flexibility in production control. It is thus also possible to childproof applicators on which the finger support is formed integrally.

The embodiment in FIGS. 4A to 4E is likewise closely related to the embodiment of FIGS. 2A to 2F. In the case of the embodiment in FIGS. 4A to 4E, the inside of the securing portion 52 of the cap unit 50 is identical to the embodiment of FIGS. 2A to 2F. This means that the securing portion 58 is likewise secured on the applicator via an inwardly directed coupling web 61b and an outwardly directed coupling groove 61a. Said sleeve portion 68b is also provided.

The particular aspect of the embodiment in FIGS. 4A to 4E lies in the childproofing itself. The cap 52 of this illustrative embodiment is designed as a double cap and has an inner cap 54a and an outer cap 54b. These two cap parts are intended to be non-separable from each other but in principle to be rotatable relative to each other. By means of mutually engaging contours 56, however, it is possible to couple the outer cap 54a to the inner cap 54b with form-fit engagement, by applying downward force to the outer cap 54b, such that a joint rotation movement is then made possible. The inside of the inner cap 54a is in turn provided with an inner thread 62b, which interacts with an outer thread 62a on the securing portion 52. It is possible, however, to omit additional blocking of rotation in accordance with FIGS. 2A to 2F. The difficulty for a child is to appreciate the connectability of the outer cap 54b and of the inner cap 54a. This accordingly prevents a child from being able in any case to introduce a torque in the area of the thread 62. An additional deformation of the cap for the purpose of separation of a rotation block is therefore not necessary.

The invention claimed is:

1. A discharge head for a dispenser for discharging a pharmaceutical or cosmetic liquid, the discharge head comprising:
   a base; and
   an applicator mounted movably on the base;
   the base is configured to be fitted onto a liquid reservoir or to be rigidly integrated on a liquid reservoir;
   the applicator comprises a discharge opening through which liquid can be released into an environment;
   a pump mechanism arranged in a liquid channel configured to connect the liquid reservoir to the discharge opening, wherein the pump mechanism can be actuated by displacement of the applicator with respect to the base; and
a childproof cap unit;
   the cap unit comprises a cap for covering the discharge opening;
the cap unit comprises a separate securing portion which is mounted on the applicator via a securing mechanism, the securing portion being releasably secured to the cap; and
   the securing portion and the cap of the cap unit are provided with a threaded mechanism for securing the cap on the securing portion.

2. The discharge head as claimed in claim 1, wherein:
   the securing portion of the cap unit comprises a body which is sleeve-shaped at least in part and is open at both ends and surrounds the applicator.

3. The discharge head as claimed in claim 1, wherein:
   the securing portion and the cap of the cap unit have an anti-rotation mechanism, by which the cap and the securing portion can be made secure against rotation, by form-fit engagement, in a defined rotation position; and
   the securing portion and the cap are deformable in part to release a rotation block of the anti-rotation mechanism.

4. The discharge head as claimed in claim 1, wherein:
   the cap comprises an inner cap and an outer cap; and
   the inner cap and the outer cap have interacting coupling means, by which a temporary rotation block between the outer cap and the inner cap can be produced by applying force to the outer cap.

5. The discharge head as claimed in claim 1, with at least one of the following:
   the securing mechanism comprises a latching connection mechanism; or
   the securing mechanism is a rotationally fixed securing mechanism, by which the securing portion and the base or the applicator are connected to each other for conjoint rotation.

6. The discharge head as claimed in claim 1, wherein:
   the securing mechanism couples the securing portion to the applicator; and
   the securing mechanism comprises a coupling web provided internally on the securing portion engaged with a radially outwardly open coupling groove.

7. The discharge head as claimed in claim 1, with at least one of the following:
   the securing portion of the cap unit has a gripping surface which, in order to increase the grippability, is provided with gripping ribs or other kinds of gripping elevations; or
   the securing portion of the cap unit comprises a finger support, which has an outer edge whose shape deviates from the shape of a circle.

8. The discharge head as claimed in claim 1, with at least one of the following:
   the applicator includes a nosepiece, at the distal end of which the discharge opening is provided; or
   the applicator is configured for releasing drops and has a drop formation surface which surrounds the discharge opening and on which emerging liquid attaches until the liquid detaches therefrom in the form of a drop; or
   the applicator has an external shape that narrows in the direction of the discharge opening, and the securing portion has a shape that narrows on the inside in a manner corresponding to the shape of the applicator; or
   the cap has, on an inside thereof, a sealing surface which, when the cap is fitted, directly closes the discharge opening.

9. The discharge head as claimed in claim 1, wherein:
   the applicator of the discharge head has a finger support; and
   the securing portion is secured on the applicator by engagement around an outside of the finger support.

10. The discharge head as claimed in claim 9, wherein:
    a circumferential sleeve portion is provided on the finger support and surrounds the base.

11. A dispenser for discharging a pharmaceutical or cosmetic liquid, the dispenser comprising:
    a liquid reservoir; and
    the discharge head according to claim 1.

12. The dispenser as claimed in claim 11, wherein:
    the liquid reservoir has a maximum volume of 100 ml.

13. A cap unit for use as part of a discharge head, the cap unit comprising:
    a securing portion for mounting on an applicator of the discharge head and a cap for covering a discharge opening of the applicator;
    the securing portion comprises a sleeve-shaped hollow body which is open at opposite ends in order to be pushed onto the applicator of the discharge head;
    the securing portion has latching means for producing a latching connection to the applicator of the discharge head;
    the cap and the securing portion are releasably secured to each other; and
    the securing portion and the cap of the cap unit are provided with a threaded mechanism for securing the cap on the securing portion.

14. A dispenser for discharging pharmaceutical liquids, the dispenser comprising:
    a liquid reservoir and a discharge head;
    the discharge head has a pump which is connected to the liquid reservoir in order to convey liquid;
    the discharge head has a base which is rigidly connected to the liquid reservoir, and an applicator which is guided linearly movably on the base and is pressed down with respect to the base for the purpose of actuating the pump and for thereby discharging liquid;
    a discharge opening through which liquid is discharged into an environment on the applicator; and
    a cap unit mounted on the applicator, the cap unit comprising a cap and a securing portion;
    the securing portion comprises a hollow body which is open at both ends and which is pushed onto the applicator from the direction of the discharge opening and is permanently secured on the applicator by a securing mechanism;
    the cap is removably secured on the securing portion to be able to be removed and placed back on again, wherein the cap, when fitted, covers the discharge opening and is made secure on the securing portion by a childproof retaining mechanism; and the securing portion and the cap of the cap unit are provided with a threaded mechanism for securing the cap on the securing portion.

* * * * *